(12) United States Patent
Altokhais

(10) Patent No.: US 9,345,512 B2
(45) Date of Patent: May 24, 2016

(54) CIRCUMCISION INSTRUMENT

(71) Applicant: Tariq Ibrahim Altokhais, Riyadh (SA)

(72) Inventor: Tariq Ibrahim Altokhais, Riyadh (SA)

( * ) Notice: Subject to any disclaimer, the term of this patent is extended or adjusted under 35 U.S.C. 154(b) by 188 days.

(21) Appl. No.: 14/267,198

(22) Filed: May 1, 2014

(65) Prior Publication Data

US 2015/0313624 A1    Nov. 5, 2015

(51) Int. Cl.
| | |
|---|---|
| *A61B 17/326* | (2006.01) |
| *A61B 18/18* | (2006.01) |
| A61B 18/14 | (2006.01) |
| A61B 18/08 | (2006.01) |
| A61B 18/00 | (2006.01) |

(52) U.S. Cl.
CPC ........... *A61B 17/326* (2013.01); *A61B 18/1815* (2013.01); *A61B 18/08* (2013.01); *A61B 18/085* (2013.01); *A61B 2018/00505* (2013.01); *A61B 2018/00589* (2013.01); *A61B 2018/00607* (2013.01); *A61B 2018/142* (2013.01); *A61B 2018/1417* (2013.01); *A61B 2018/1462* (2013.01)

(58) Field of Classification Search
CPC ....................... A61B 17/326; A61B 2018/1417; A61B 18/08; A61B 18/085; A61B 18/1815; A61B 2018/00589; A61B 2018/142; A61B 2018/00607; A61B 2018/1462; A61B 2018/00505
See application file for complete search history.

(56) References Cited

U.S. PATENT DOCUMENTS

| | | | |
|---|---|---|---|
| 1,256,208 A | 2/1918 | Cummins | |
| 1,765,319 A * | 6/1930 | Williams | A61B 17/326 606/118 |
| 2,294,852 A * | 9/1942 | Smith | A61B 17/326 606/113 |
| 2,548,670 A * | 4/1951 | Hyatt | A61B 17/326 606/118 |
| 3,013,560 A * | 12/1961 | Cohen | A61B 17/326 606/118 |
| 3,072,126 A * | 1/1963 | Fenton | A61B 17/326 606/118 |
| 3,111,124 A | 11/1963 | Rodbard | |
| 3,625,218 A | 12/1971 | Valinoti, Jr. | |
| 3,651,811 A * | 3/1972 | Hildebrandt | A61B 17/3201 606/51 |

(Continued)

OTHER PUBLICATIONS www.aesculapusa.com/assets/base/doc/DOC840-Bipolar_Surgery_Brochure.pdf; Instruments and Devices for Bipolar Surgery Brochure from Aesculap; Received & Printed on May 21, 2012.

(Continued)

*Primary Examiner* — Jing Ou
(74) *Attorney, Agent, or Firm* — Neustel Law Offices; Michael S. Neustel

(57) ABSTRACT

A circumcision instrument used to perform a circumcision procedure. The circumcision instrument generally includes a housing having a chamber configured to receive a glans penis and an outer surface configured to be enveloped by a prepuce. An annular groove is disposed in the outer surface. A conductive ring is located at the bottom of the annular groove. A clamp has a pair of jaws that are moveable from an open position to a closed position surrounding the prepuce. In the closed position the jaws are disposed at least partially within the annular groove. A conductive inner cutting edge is located on the jaws. The clamp and the housing are connectable to a source of diathermy energy such that diathermy energy can flow between the inner cutting edge and the conductive ring, thereby cutting the prepuce.

33 Claims, 10 Drawing Sheets

(56) References Cited

U.S. PATENT DOCUMENTS

| | | | |
|---|---|---|---|
| 3,741,215 A | 6/1973 | Ayad | |
| 4,491,136 A * | 1/1985 | LeVeen | A61B 17/326 606/118 |
| 5,649,933 A | 7/1997 | Singh | |
| 5,797,921 A * | 8/1998 | Cimini | A61B 17/326 606/118 |
| 6,254,613 B1 | 7/2001 | Harrison | |
| 2003/0171747 A1 | 9/2003 | Kanehira | |
| 2004/0153020 A1 * | 8/2004 | Bartel | A61B 18/1442 604/1 |
| 2008/0004654 A1 * | 1/2008 | Tomlinson | A61B 17/326 606/201 |
| 2010/0004644 A1 | 1/2010 | Zipper | |
| 2012/0203242 A1 | 8/2012 | Fuerst | |
| 2013/0197536 A1 | 8/2013 | Singh | |

OTHER PUBLICATIONS

PCT International Search Report from the International Searching Authority; Received and Printed on Mar. 14, 2015.

PCT Written Opinion of the International Searching Authority; Received and Printed on Mar. 14, 2015.

* cited by examiner

CIRCUMCISION INSTRUMENT

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to surgical instruments and more specifically it relates to a circumcision instrument for performing a circumcision procedure.

2. Description of the Related Art

Any discussion of the related art throughout the specification should in no way be considered as an admission that such related art is widely known or forms part of common general knowledge in the field.

Male circumcision is one of the most commonly performed operations worldwide. Approximately 30% of men globally and 35% of men in developing countries are circumcised for religious, cultural, medical and other reasons, such as hygiene, aesthetics and peer pressure. Circumcision prevents not only urinary tract infections in infants, but also sexually transmitted diseases and cervical and penile cancer in adults. The World Health Organization, the Joint United Nations Program on HIV/AIDS and the US President's Emergency Plan for AIDS Relief have identified male circumcision as an effective means of HIV prevention in regions with high rates of heterosexual transmission. Male circumcision has been performed using many different techniques; at different age groups; with or without anesthesia; by medical and non-medical personnel. Each technique has its advantages and disadvantages. If circumcision is to be performed in the out-patient clinic under local anesthesia, the technique used should be safe and fast. Numerous techniques for male circumcision have been used, such as conventional circumcision, the Shenghuan Disposable Minimally Invasive Circumcision Anastomosis device, the plastic clamp technique and the Plastibell device.

Regardless of which method is selected, there are complications. The most common complication is bleeding. The Plastibell device is the most frequently used circumcision device in the world. It has to be worn for several days. There are also other complications of the Plastibell device, including the delayed separation of the ring, bleeding, localized superficial infection and proximal migration of the ring. If the Plastibell device does not release, complications can result such as penile edema and penile ischemia. In addition, some unusual complications may occur such as ischemic glans penis, urine retention and grievous penile injury as well as parental/care giver anxiety until the device falls off.

Because of the inherent problems with the related art, there is a need for an improved circumcision instrument for use in performing circumcision procedures.

BRIEF SUMMARY OF THE INVENTION

The invention generally relates to a circumcision instrument for performing a circumcision procedure. The circumcision instrument includes a housing having a chamber configured to receive a glans penis and an outer surface configured to be enveloped by a prepuce. An annular groove is disposed in the outer surface. A conductive ring is located at the bottom of the annular groove. A clamp has a pair of jaws that are moveable from an open position to a closed position surrounding the prepuce. In the closed position, the jaws are disposed at least partially within the annular groove. A conductive inner cutting edge is located on the jaws. The clamp and the housing are connectable to a source of diathermy energy such that diathermy energy can flow between the inner cutting edge and the conductive ring, thereby cutting the prepuce.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

Figure 1:
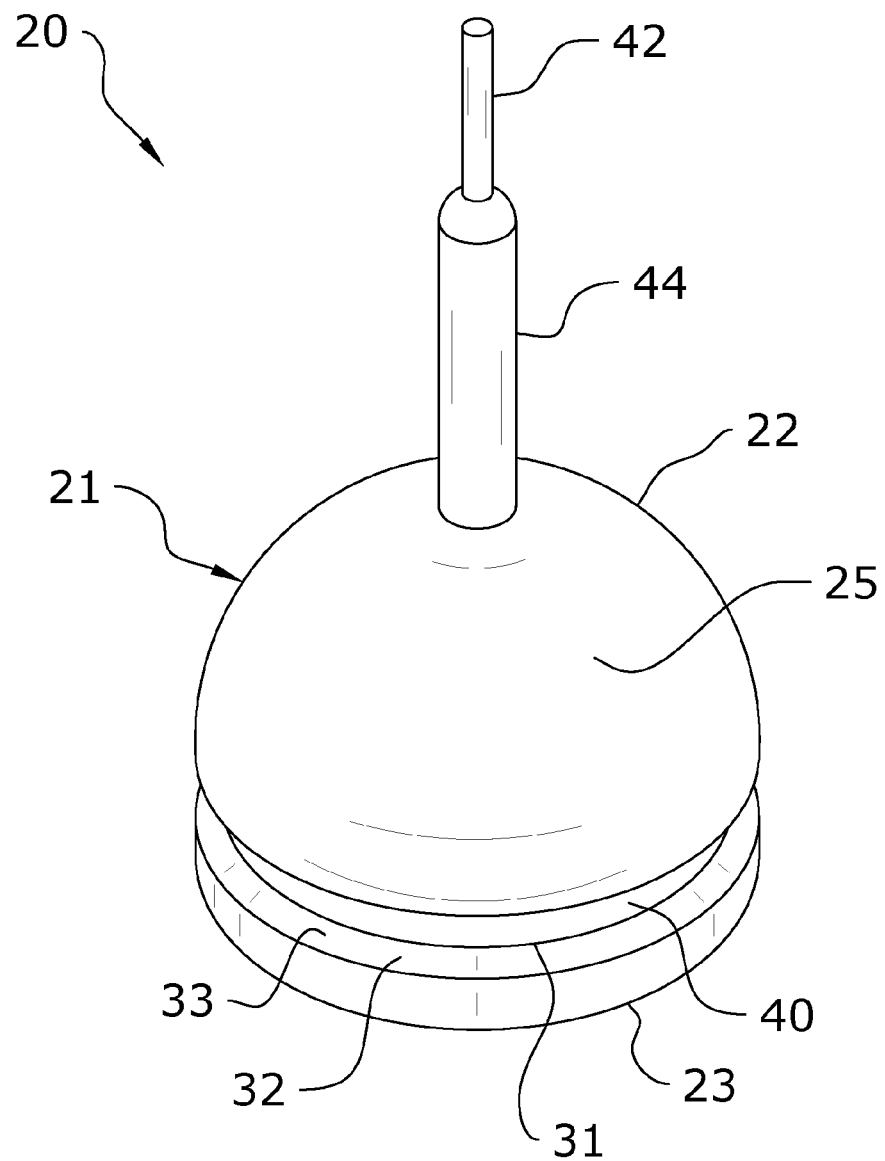
FIG. 1 is an overall upper front perspective view of a circumcision housing of the present invention.
Figure 2:
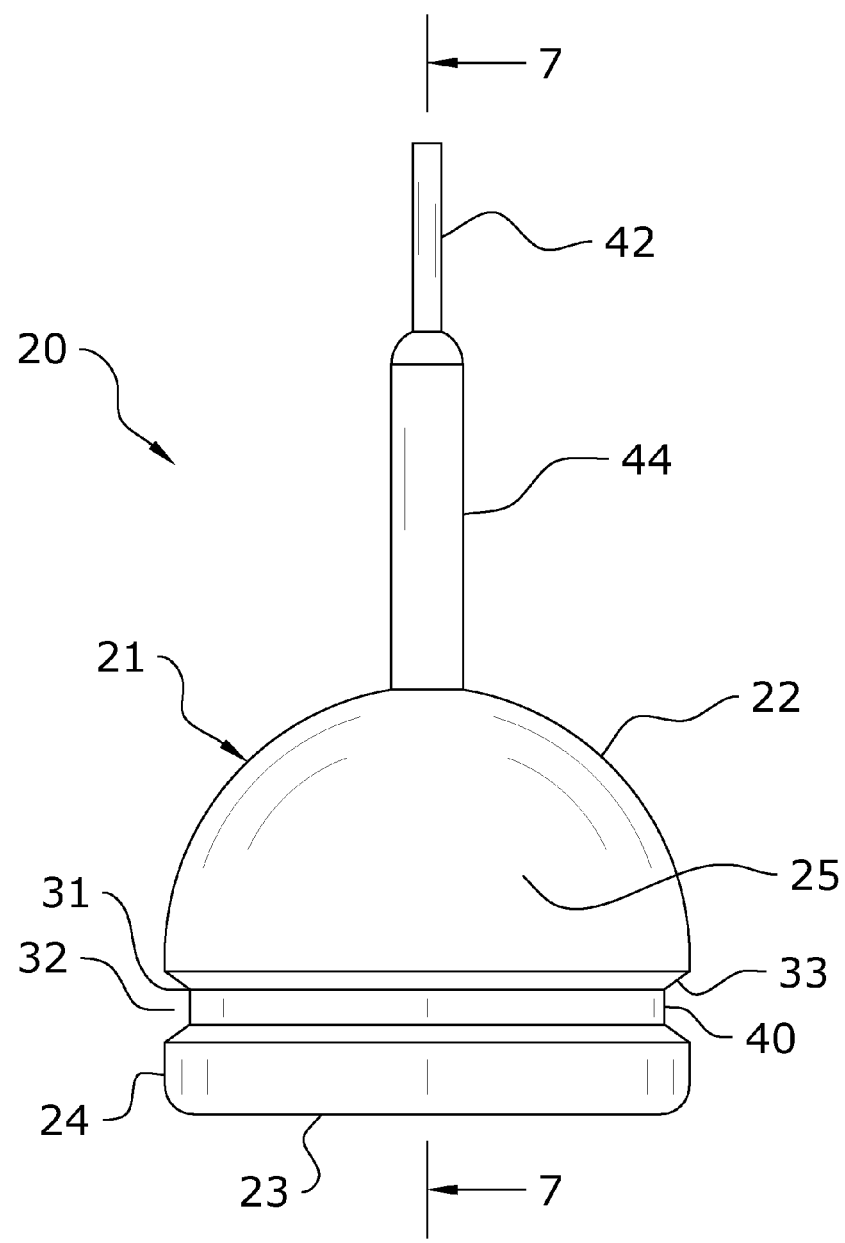
FIG. 2 is a side view of the circumcision housing.
Figure 3:
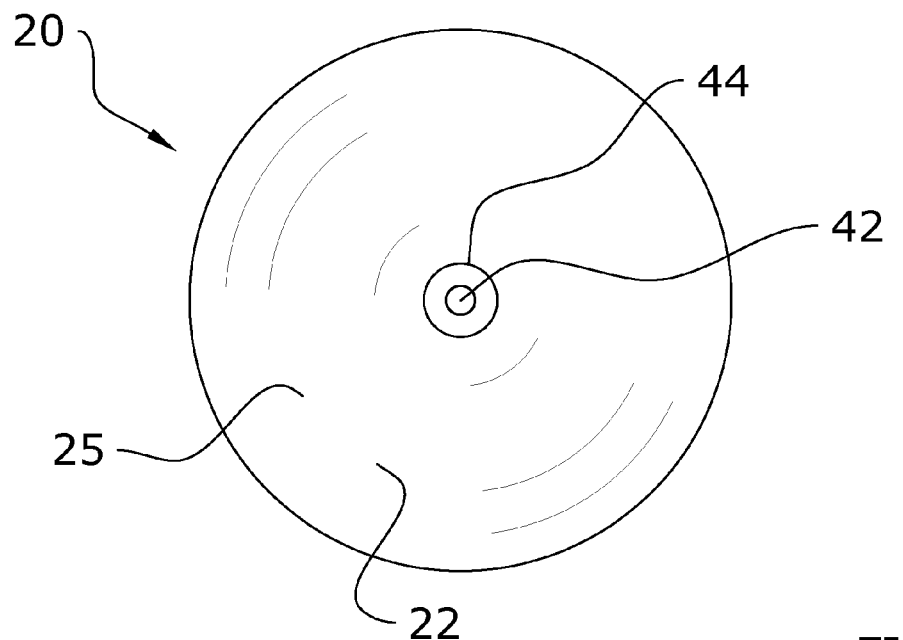
FIG. 3 is a top view of the circumcision housing.
Figure 4:
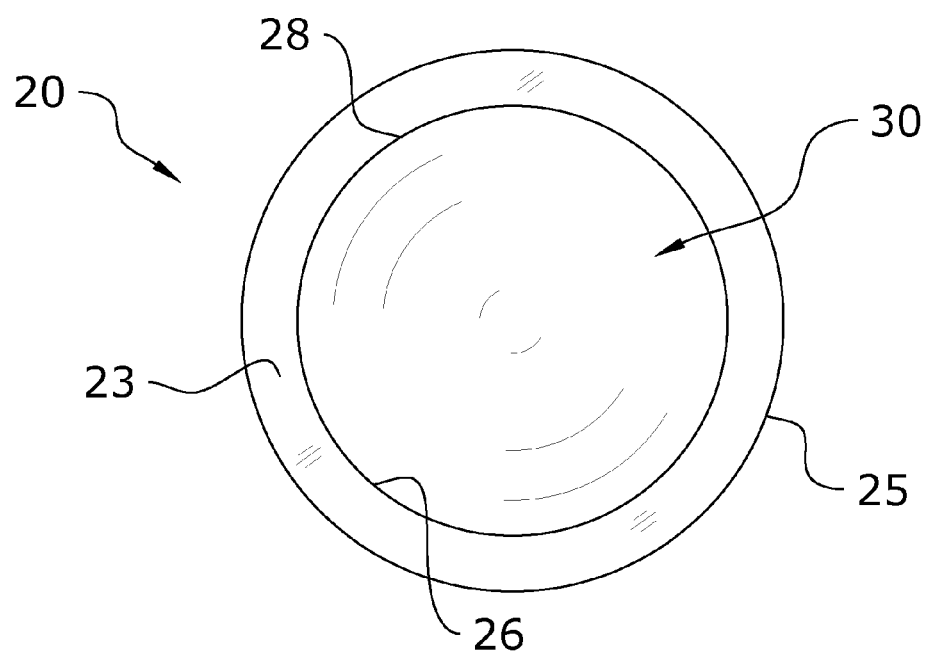
FIG. 4 is a bottom view of the circumcision housing.
Figure 5:
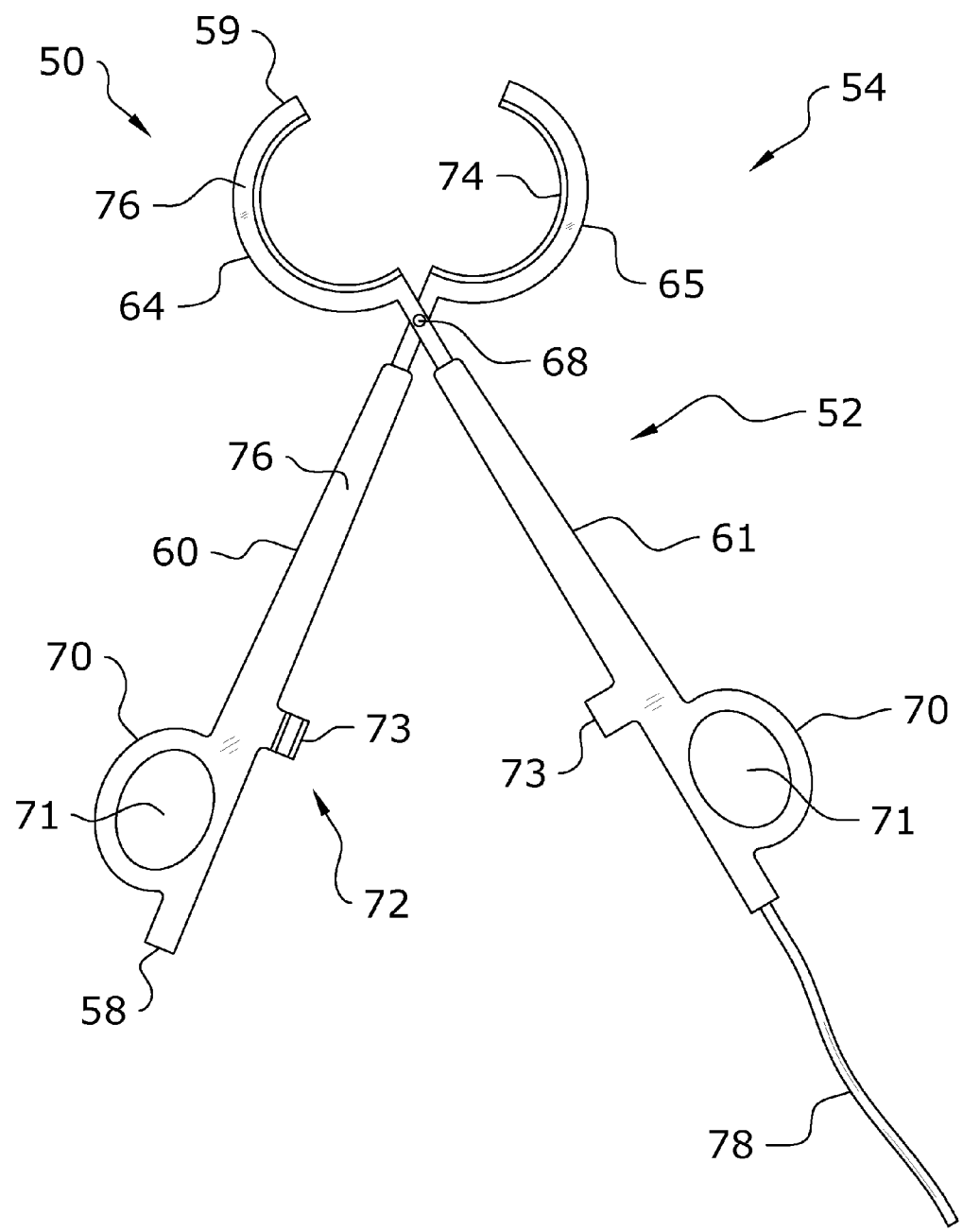
FIG. 5 is a top view of a circumcision clamp of the present invention in an open position.
Figure 6:
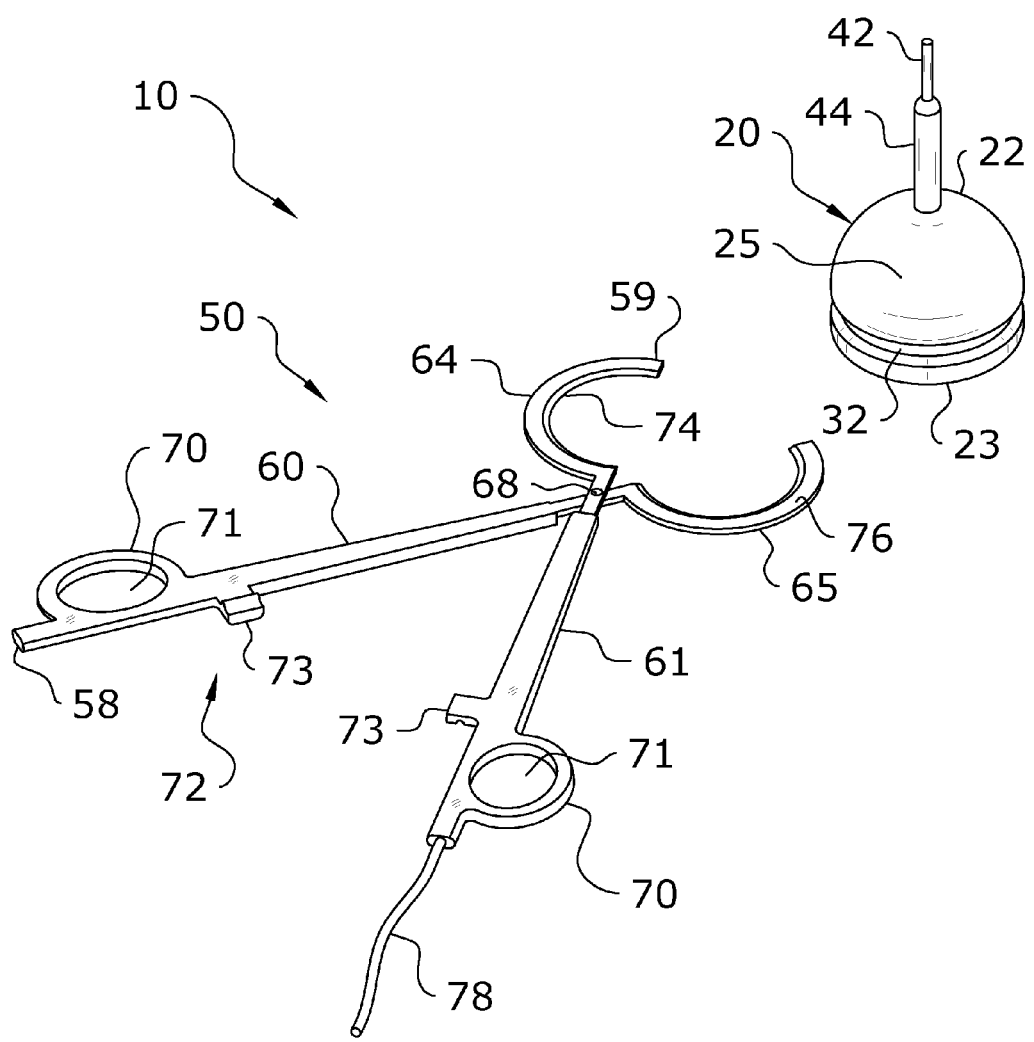
FIG. 6 is an overall upper front perspective view illustrating both the circumcision housing and the circumcision clamp in an open position.

A. Overview.

Turning now descriptively to the drawings, in which similar reference characters denote similar elements throughout the several views, FIGS. 1 through 10b illustrate a circumcision instrument 10 for performing a circumcision procedure. The circumcision instrument 10 comprises a circumcision housing 20 having a chamber 30 configured to receive a glans penis 102 and an outer surface 25 configured to be enveloped by a foreskin or prepuce 104. An annular groove 32 is disposed in the outer surface 25. A conductive ring 40 is located at the bottom 31 of the annular groove 32. A clamp 50 has a pair of jaws 64, 65 that are moveable from an open position 54 to a closed position 56 surrounding the prepuce 104. In the closed position, the jaws 64, 65 are disposed at least partially within the annular groove 32. In one embodiment, the jaws 64, 65 are located entirely within the annular groove 32. A conductive inner cutting edge 74 is located on the jaws 64, 65. The clamp 50 and the housing 20 are connectable to a diathermy machine 90 that supplies diathermy energy. The diathermy energy flows between the inner cutting edge 74 and the conductive ring 40, thereby cutting the prepuce 104.

B. Circumcision Housing.

FIGS. 1 through 4 illustrate the circumcision housing 20. The circumcision housing 20 is generally hemi-spherical in shape. The circumcision housing 20 has a main body 21, a top 22, a bottom 23, an outer peripheral wall 24, an outer surface 25, and an inner surface 26. An opening 28 is located at the bottom 23 and opens into a hemi-spherical internal chamber 30 formed within housing 20. An annular groove 32 has angled walls 33 that extend inwardly into outer wall 24. The annular groove 32 has a bottom 31 at the end of angled walls 33.

Figure 9:
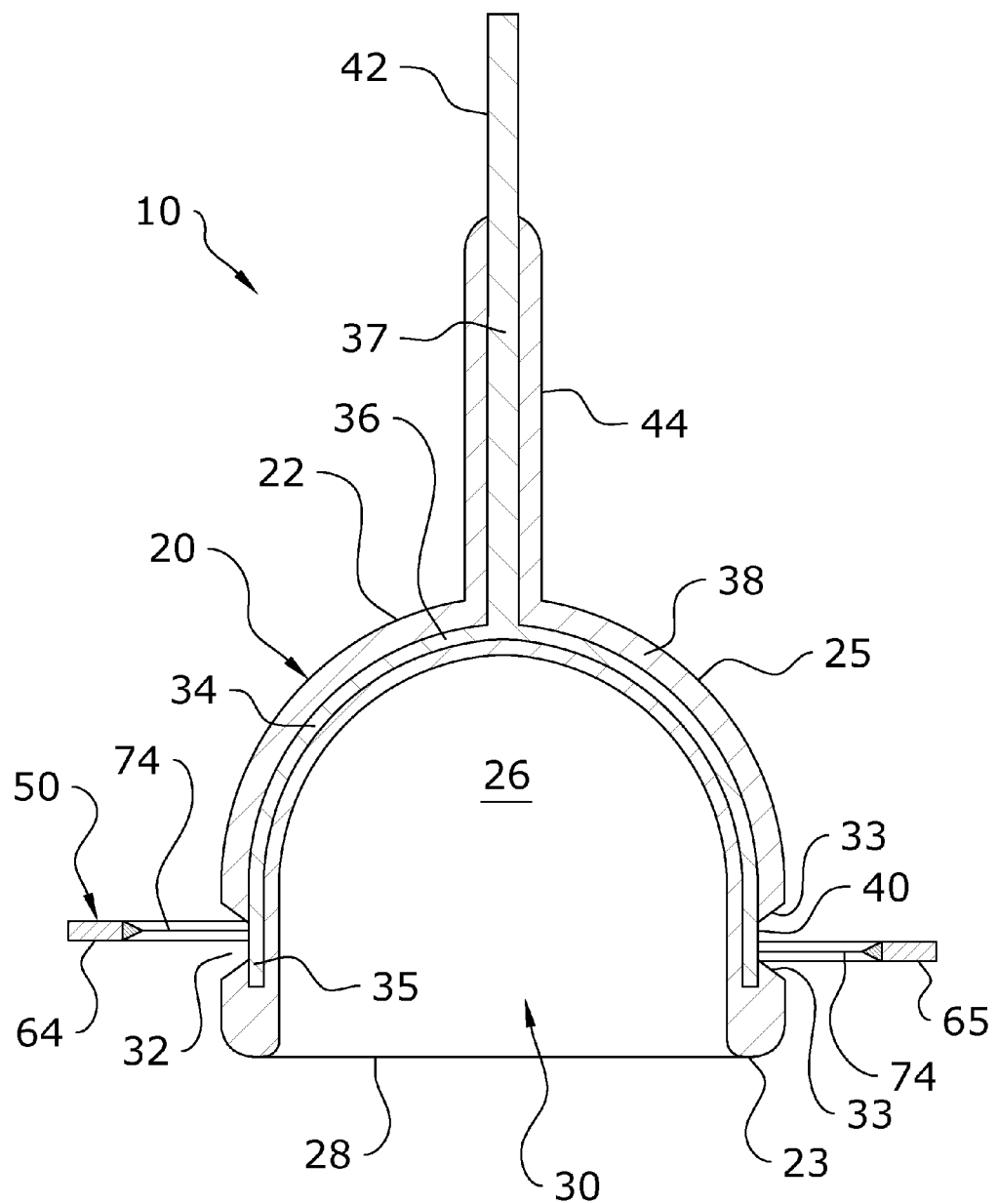
FIG. 9 is a side cross-sectional view of the circumcision housing taken along section line 9-9 of FIG. 2 and a side cross-sectional view of the circumcision clamp in the open position.

With additional reference to FIG. 9, the circumcision housing 20 further includes a hemi-spherical shaped conductive cone 34 disposed within the housing 20. The conductive cone 34 can be formed from an electrically conductive material such as a metal. The conductive cone 34 has a bottom portion 35, top portion 36 and a connecting member 37 that is attached to top portion 36. An insulating cover 38 is disposed over the outer and inner surfaces of cone 34. The insulating cover 38 is formed from an electrically non-conductive material such as but not limited to rubber or plastic. The insulating cover 38 forms the outer 25 and inner 26 surfaces of the housing 20. The insulating cover 38 is absent from the bottom 31 of the annular groove 32 such that an annular conductive ring 40 of the conductive cone 34 is exposed around the entire circumference of the housing 20. The insulating cover 38 is also absent from the distal end of the connecting member 37 such that a terminal 42 is exposed. Where the insulating cover 38 covers the proximal portion of connecting member 37, a handle 44 is formed. The handle 44 allows a surgical practitioner to manipulate and position the circumcision housing 20.

C. Circumcision Clamp.

Referring to FIGS. 5 through 8, the circumcision instrument 10 further comprises a circumcision clamp 50. The circumcision clamp 50 has a scissors mechanism 52 that allows the circumcision clamp 50 to be moved between an open position 54 and a closed position 56. The circumcision clamp 50 can be formed from a suitable material such as stainless steel. The circumcision clamp 50 includes a proximal end 58, a distal end 59, arms 60, 61 and jaws 64, 65. A pivot pin 68 rotatably connects the arms 60, 61 for pivoting movement of each arm about pivot pin 68. Finger loops 70 and finger holes 71 are integrally formed with arms 60, 61 toward the proximal end 58. Finger loops 70 and holes 71 allow a surgical practitioner to grasp and manipulate the clamp 50. A locking mechanism 72 is attached to opposed portions of the arms 60, 61. The locking mechanism 72 has interlocking clips 73 that engage each other in the closed position 56 to retain the clamp 50 in the closed position 56.

The circumcision clamp 50 further includes a jaw 64 that is connected to the distal end of an arm 61 and a jaw 65 that is connected to the distal end of an arm 60. The jaws 64, 65 are semi-circular in shape and can be moved toward and away from each other by the complementary movement of the arms 60, 61 toward and away from each other by a user. The inner most surface of the jaws 64, 65 are formed with a conductive inner cutting edge 74. The remainder of the jaws 64, 65 and the rest of circumcision clamp 50 can be covered with an insulating coating 76. The insulating coating 76 is electrically insulating and non-conductive. An electrically conductive wire 78 is attached to the proximal end 58 of one of the arms 61. The wire 78 is electrically connected to the clamp 50.

D. Diathermy Machine.

Figure 7:
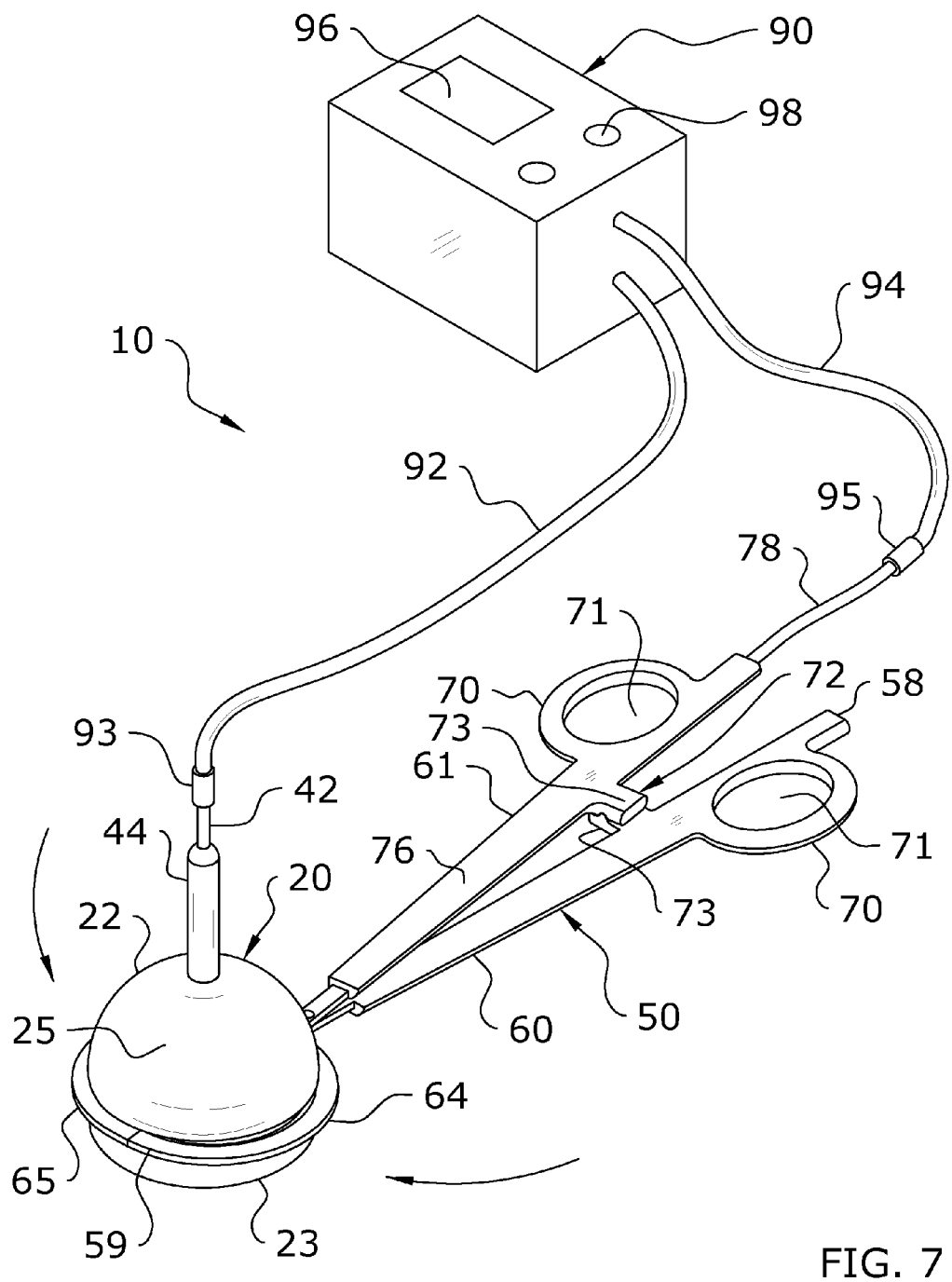
FIG. 7 is an overall upper front perspective view illustrating the circumcision housing with the circumcision clamp attached in a closed position.
Figure 8:
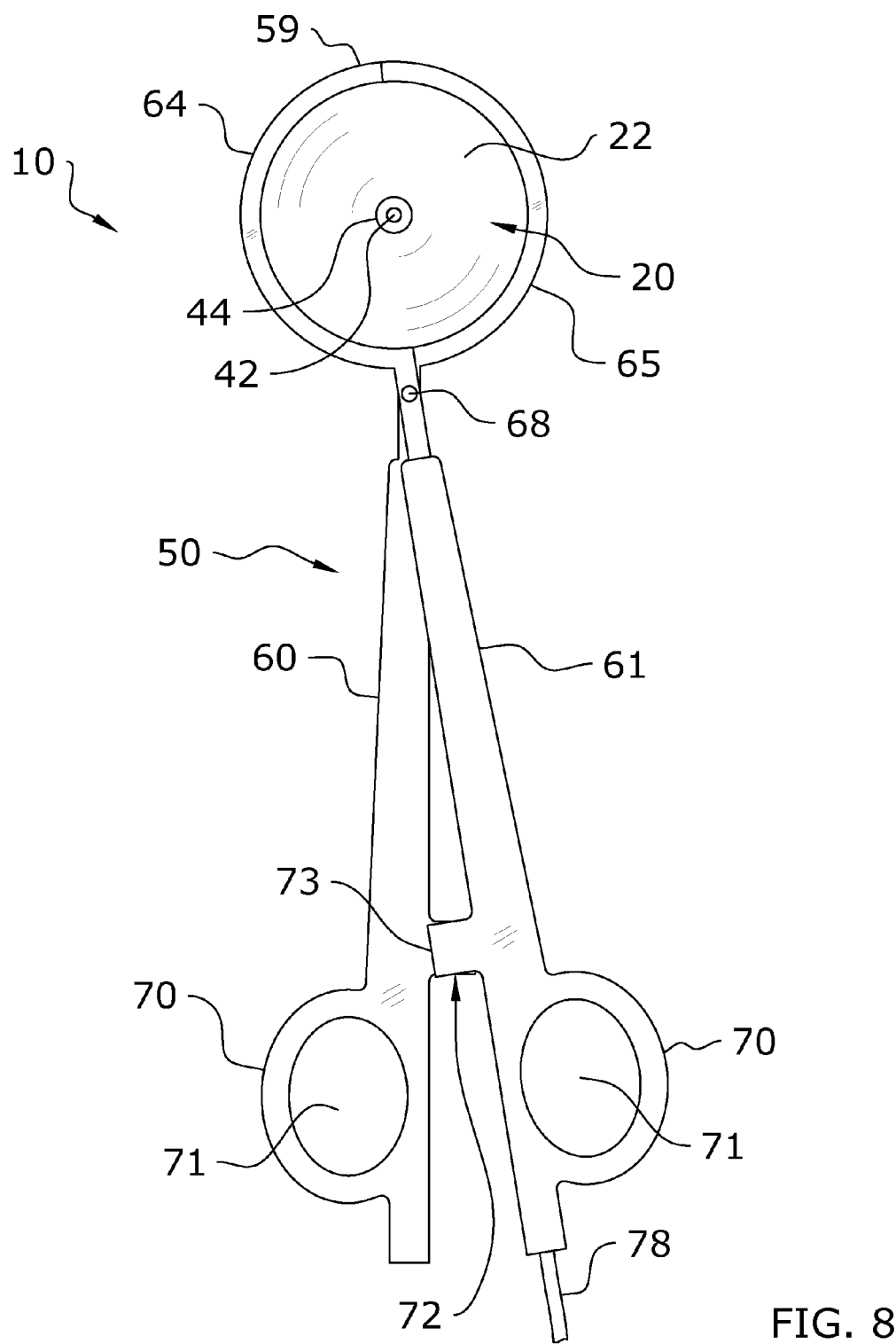
FIG. 8 is a top view of the circumcision clamp in a closed position.

Referring to FIG. 7, the circumcision instrument 10 is shown connected to a diathermy machine 90. The diathermy machine 90 is a source of diathermy energy to the circumcision instrument 10. Diathermy means dielectric heating produced by rotation of molecular dipoles in a high frequency alternating electric field. This effect is most widely used in microwave ovens. The diathermy machine 90 generates electromagnetic waves that can vary in wavelength from microwaves to radio frequency waves. The diathermy machine 90 is used in electro-surgery. Electro-surgery refers broadly to a class of medical procedures that rely on the application of high frequency electrical energy to patient tissue to achieve a number of possible effects, such as cutting, coagulation, hyperthermia and necrosis. Electro-surgical devices rely on contacting electrodes of different polarity in close proximity to each other against a human tissue.

The diathermy machine 90 is electrically connected to the housing 20 by a wire 92 and a connector 93 connected to a terminal 42. The diathermy machine 90 is electrically connected to the clamp 50 by a wire 94 and a connector 95 that is connected to a wire 78. The diathermy machine 90 includes a display 96 that provides information relating to the operation of the diathermy machine 90 such as the output frequency and duration of the energy pulse. The diathermy machine 90 further includes input control devices 98 such as buttons and knobs that allow the user to control the operational settings of the diathermy machine 90 such as the output frequency and duration of the energy pulse.

E. Method of Operation.

Figure 10A:
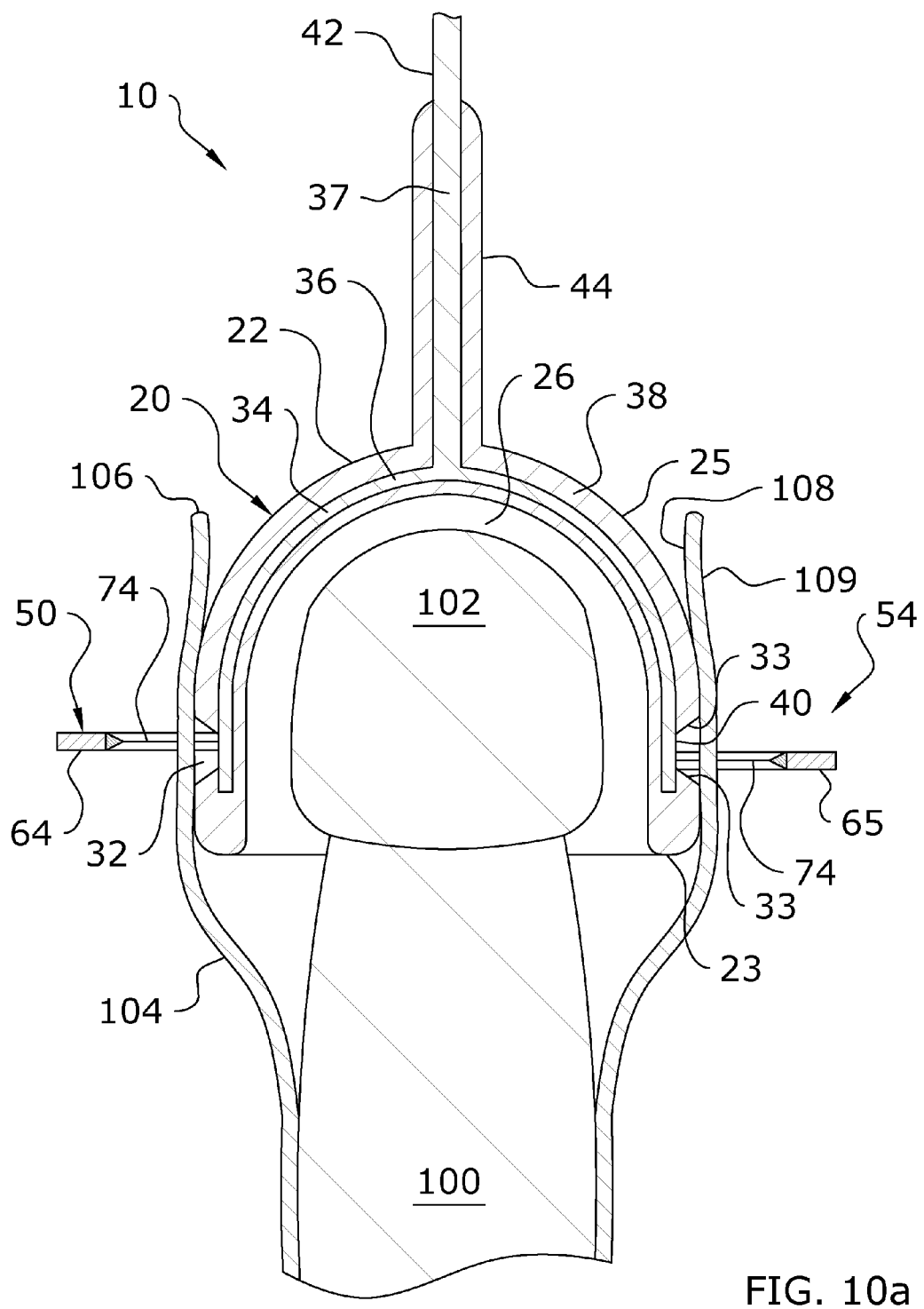
FIG. 10a is a side cross-sectional view of the circumcision housing after receving a glans penis with the prepuce extending over the housing and the circumcision clamp in the open position.

Referring to FIG. 7, a surgical practitioner begins a circumcision procedure by connecting the connector 93 to the terminal 42 of the housing 20 and connecting the connector 95 to the wire 78 that is attached to clamp 50, thereby connecting the diathermy machine 90 to the circumcision instrument 10. Turning to FIG. 9, initially the circumcision housing 20 is empty and the clamp 50 is in an open position 54. It is noted that circumcision housing 20 and clamp 50 can be manufactured in a range of appropriate sizes and that the surgical practitioner can select the appropriate sizes of circumcision housing 20 and clamp 50 to be used. With reference to FIG. 10a, the surgical practitioner grasps the handle 44 and positions the housing 20 over the glans penis 102 located at the end of the penis 100. In this position, the glans penis 102 is located within the chamber 30 and surrounded by the inner surface 26. The foreskin or prepuce 104 is positioned by the surgical practitioner over the outer surface 25 such that the housing 20 is enveloped by the prepuce 104 as shown in FIG.

10a. The prepuce 104 has an end portion 106. A portion of the prepuce inner surface 108 is in contact with the outer surface 25. The housing 20 is therefore located between the glans penis 102 and the prepuce 104.

Figure 10B:
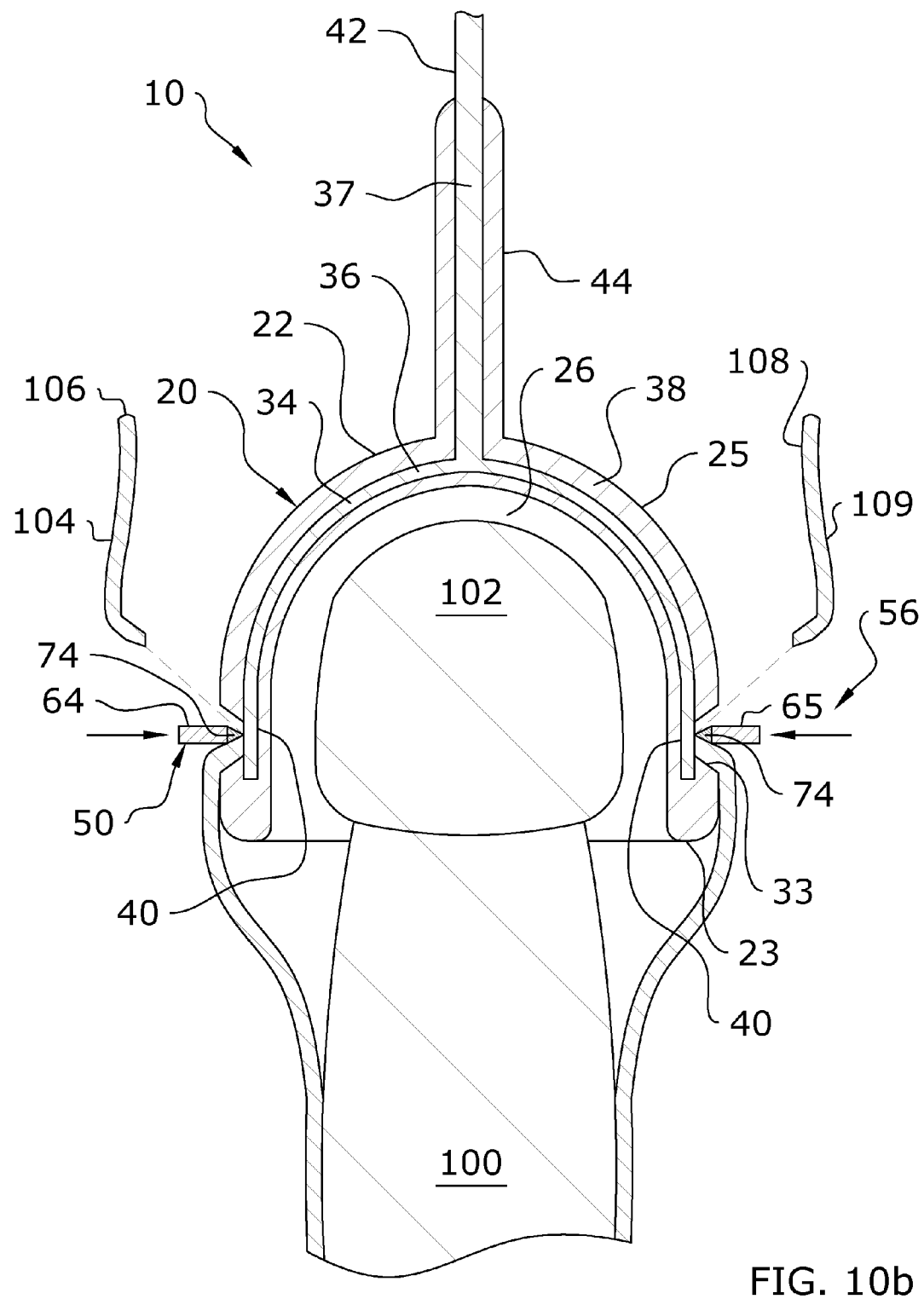
FIG. 10b is a side cross-sectional view of the circumcision housing after receving a glans penis with the circumcision clamp in the closed position illustrating resection of the prepuce.

Next, the surgical practitioner positions the clamp 50 around the housing 20. With the jaws 64, 65 in the open position 54, the jaws 64, 65 are moved to a position juxtaposed to the annular groove 32. The surgical practitioner, while grasping the finger loops 70, squeezes the arms 60, 61 towards each other causing the jaws 64, 65 to move toward the prepuce 104. Further squeezing of the arms 60, 61, by the surgical practitioner, causes the inner cutting edges 74 to come into contact with the prepuce 104 and to bend a portion of the prepuce 104 into the annular groove 32 and into contact with the conductive ring 40. In this position, the jaws 64, 65 are disposed at least partially within the annular groove 32 of the housing 20. In one embodiment, the jaws 64, 65 are located entirely within the annular groove 32. Additional squeezing of the arms 60, 61, by the surgical practitioner, causes opposed clips 73 (FIG. 5) of the locking mechanism 72 to engage thereby locking the jaws 64, 65 in the annular groove 32 and surrounding the contact ring 40. This is the closed position 56 as shown in FIG. 10b.

The next step in the circumcision procedure is for the surgical practitioner to trigger the diathermy machine 90 to supply diathermy energy that flows between the inner cutting edges 74 and the conductive ring 40, thereby cutting the prepuce 104. The high frequency electrical current flows from the inner cutting edge 74 of each jaw through the foreskin tissue 104 and into conductive ring 40. By energizing the inner cutting edges 74 and conductive ring 40 at opposite polarities using the diathermy machine 90, the foreskin 104 located between the inner cutting edges 74 and the ring 40, will be coagulated and excised or resected. During the circumcision procedure, skin adjacent to the prepuce 104 is protected from excess heat by the insulating coating 76 on the outer surface of the jaws 64, 65 and the remainder of the clamp 50. The insulating coating 76 also prevents heating of the clamp 50 in order to be safe for the surgical practitioner to handle.

After the prepuce 104 has been separated, the surgical practitioner unlocks the clamp 50 by moving the clips 73 away from each other along an axis perpendicular to the axis of the arms 60, 61. The surgical practitioner moves the clamp 50 from the closed position 56 to the open position 54 and removes the housing 20 from the glans penis 102.

The use of the circumcision instrument 10 has several advantages. First, the housing 20 and the clamp 50 are readily positioned by a surgical practitioner resulting in a fast circumcision procedure. Second, the use of diathermy energy results in cutting the foreskin 104 in a precise pure regular circular incision without bleeding. Third, the use of the housing 20 and the clamp 50 limits the effect of the diathermy energy to the tissue held between the housing 20 and the clamp 50 and fourth, the glans penis 102 is protected from electrical and thermal injuries by the insulating cover 38.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A circumcision instrument comprising:
    a housing having a chamber and an outer surface;
    an annular groove disposed in the outer surface;
    a conductive ring located at the bottom of the annular groove;
    an insulating cover disposed over the housing, except in the annular groove such that the conductive ring is exposed;
    the chamber configured to receive a glans penis and the outer surface configured to be enveloped by a prepuce; and
    a clamp having a pair of jaws wherein, the jaws are moveable from an open position to a closed position surrounding the prepuce and wherein in the closed position the jaws are disposed at least partially within the annular groove.

2. The circumcision instrument of claim 1, wherein the jaws each have an inner cutting edge located thereon.

3. The circumcision instrument of claim 2, wherein the inner cutting edge is conductive.

4. The circumcision instrument of claim 3, wherein the clamp and the housing are connectable to a source of diathermy energy such that diathermy energy can flow between the inner cutting edge and the conductive ring, thereby cutting the prepuce.

5. The circumcision instrument of claim 2, wherein a wire is connected to one end of the clamp, the wire being electrically connected to an inner cutting edge of one of the jaws through the clamp.

6. The circumcision instrument of claim 1, wherein the housing further comprises:
    a handle connected to the housing and extending away from the housing; and
    a conductive cone disposed within the housing.

7. The circumcision instrument of claim 6, wherein a conductive member extends through the handle and is connected to the conductive cone.

8. The circumcision instrument of claim 1, wherein the clamp further comprises:
    a pair of opposed arms moveably coupled to a pivot pin; and
    the jaws coupled to a respective end of the arms such that pivoting movement of the arms about the pivot pin causes the jaws to move between the open and closed positions.

9. The circumcision instrument of claim 1, wherein the clamp is formed from a conductive material and is at least partially covered by an insulating coating.

10. The circumcision instrument of claim 1, wherein a locking mechanism is mounted to the clamp, the locking mechanism configured to hold the clamp in the closed position.

11. An instrument for performing a circumcision procedure comprising:
    a housing having a chamber configured to receive a glans penis and an outer surface configured to be enveloped by a prepuce;
    an annular groove disposed in the outer surface;
    a conductive ring located at the bottom of the annular groove;
    an insulating cover disposed over the housing, except in the annular groove such that the conductive ring is exposed;

a clamp having a pair of jaws wherein, the jaws are moveable from an open position to a closed position surrounding the prepuce and wherein in the closed position the jaws are disposed at least partially within the annular groove; and a conductive inner cutting edge located on the jaws.

12. The instrument of claim 11, wherein the clamp and the housing are connectable to a source of diathermy energy such that diathermy energy can flow between the inner cutting edge and the conductive ring, thereby cutting the prepuce.

13. The instrument of claim 11, wherein the housing further comprises:

a handle connected to the housing and extending away from the housing; and a conductive cone disposed within the housing.

14. The instrument of claim 11, wherein the clamp further comprises:

a pair of opposed arms moveably coupled to a pivot pin; and the jaws coupled to a respective end of the arms such that pivoting movement of the arms about the pivot pin causes the jaws to move between the open and closed positions.

15. The circumcision instrument of claim 11, wherein a locking mechanism is mounted to the clamp, the locking mechanism configured to hold the clamp in the closed position.

16. A circumcision system, comprising:

a housing having an opening within an end of the housing and a chamber connected to the opening, wherein the chamber is configured to receive a glans penis, wherein an outer surface of the housing is configured to be at least partially enveloped by a prepuce, wherein the housing is comprised of:

a conductive member having an exterior surface and an interior surface opposite of the exterior surface, wherein the conductive member is formed from an electrically conductive material;

an insulating cover disposed over at least a portion of the exterior surface of the conductive member; and an annular groove extending through the insulating cover exposing a portion of the exterior surface of the conductive member; and a clamp having a pair of jaws, wherein each of the jaws includes a conductive inner cutting edge, the jaws are adapted to be moveable from an open position to a closed position surrounding the prepuce, wherein when in the closed position the conductive inner cutting edge of each of the jaws is disposed at least partially within the annular groove.

17. The circumcision system of claim 16, wherein the clamp and the conductive member are adapted to be connectable to a source of diathermy energy such that diathermy energy can flow between the conductive inner cutting edge and the portion of the exterior surface of the conductive member exposed within the annular groove.

18. The circumcision system of claim 16, including a source of diathermy energy, wherein the clamp and the conductive member are electrically connected to the source of diathermy energy such that diathermy energy flows between the conductive inner cutting edge and the portion of the exterior surface of the conductive member exposed within the annular groove.

19. The circumcision system of claim 16, wherein the annular groove tapers inwardly.

20. The circumcision system of claim 16, wherein the insulating cover is disposed over at least a portion of the interior surface of the conductive member.

21. The circumcision system of claim 16, wherein the conductive member is comprised of a semi-spherical structure.

22. A circumcision instrument comprising:

a housing having a chamber and an outer surface;
an annular groove disposed in the outer surface;
wherein the housing further comprises:

a handle connected to the housing and extending away from the housing;

a conductive cone disposed within the housing; and an insulating cover disposed over the housing, except in the annular groove such that the conductive ring is exposed;

the chamber configured to receive a glans penis and the outer surface configured to be enveloped by a prepuce; and a clamp having a pair of jaws, the jaws are moveable from an open position to a closed position surrounding the prepuce and wherein in the closed position the jaws are disposed at least partially within the annular groove.

23. The circumcision instrument of claim 22, wherein the jaws each has an inner cutting edge located thereon.

24. The circumcision instrument of claim 23, wherein the inner cutting edge of each jaw is conductive.

25. The circumcision instrument of claim 24, wherein the clamp and the housing are connectable to a source of diathermy energy such that diathermy energy can flow between the inner cutting edge and the conductive ring, thereby cutting the prepuce.

26. The circumcision instrument of claim 22, wherein the housing comprises a handle connected to the housing and extending away from the housing.

27. The circumcision instrument of claim 22, wherein a conductive member extends through the handle and is connected to the conductive cone.

28. The circumcision system of claim 22, wherein the conductive cone is comprised of a semi-spherical structure.

29. The circumcision instrument of claim 22, wherein the clamp is comprised of:

a pair of opposed arms moveably coupled to a pivot pin; and the jaws coupled to a respective end of the arms such that pivoting movement of the arms about the pivot pin causes the jaws to move between the open and closed positions.

30. The circumcision instrument of claim 22, wherein the clamp is formed from a conductive material and is at least partially covered by an insulating coating.

31. The circumcision instrument of claim 30, wherein a wire is connected to one end of the clamp, the wire being electrically connected to an inner cutting edge of one of the jaws through the clamp.

32. The circumcision instrument of claim 22, wherein the clamp includes a pair of arms connected to the jaws and a pair of interlocking members extending from arms, wherein the interlocking members engage each other in the closed position to retain the clamp in the closed position.

33. The circumcision system of claim 22, including a source of diathermy energy, wherein the clamp and the conductive cone are electrically connected to the source of diathermy energy such that diathermy energy flows between the conductive inner cutting edge and the portion of the exterior surface of the conductive member exposed within the annular groove.

* * * * *